(12) United States Patent
Keller, III et al.

(10) Patent No.: US 12,379,329 B2
(45) Date of Patent: Aug. 5, 2025

(54) RF RAPID DIAGNOSTICS OF INFECTION AND CONTAMINATION

(71) Applicant: NOKOMIS, INC., Canonsburg, PA (US)

(72) Inventors: Walter J Keller, III, Bridgeville, PA (US); James Robert Uplinger, II, Cranberry Township, PA (US); Vladimir Makarenko, McDonald, PA (US)

(73) Assignee: Nokomis, Inc., Canonsburg, PA (US)

( * ) Notice: Subject to any disclaimer, the term of this patent is extended or adjusted under 35 U.S.C. 154(b) by 901 days.

(21) Appl. No.: 16/857,945

(22) Filed: Apr. 24, 2020

(65) Prior Publication Data

US 2021/0333222 A1 Oct. 28, 2021

(51) Int. Cl.
*G01N 22/00* (2006.01)
*G01N 33/497* (2006.01)

(52) U.S. Cl.
CPC ........... *G01N 22/00* (2013.01); *G01N 33/497* (2013.01)

(58) Field of Classification Search
CPC ....... G01N 22/00; G01N 33/497; A61B 5/087
See application file for complete search history.

(56) References Cited

U.S. PATENT DOCUMENTS

| | | | |
|---|---|---|---|
| 3,973,186 A | 8/1976 | Uehara | |
| 5,723,055 A | 3/1998 | Janssen | |
| 5,824,271 A | 10/1998 | Frank | |
| 5,949,237 A | 9/1999 | Berger | |
| 6,210,464 B1 | 4/2001 | Nakanishi | |
| 6,255,808 B1 | 7/2001 | Hucker | |
| 9,851,386 B2 | 12/2017 | Keller et al. | |
| 10,408,850 B1* | 9/2019 | Gordon | C07D 407/12 |
| 10,448,864 B1 | 10/2019 | Uplinger, II et al. | |
| 2005/0039743 A1 | 2/2005 | Taylor | |
| 2008/0030357 A1* | 2/2008 | Lueck | G01N 33/4972 600/529 |
| 2010/0123453 A1* | 5/2010 | Pauly | G01R 29/0871 324/76.11 |
| 2012/0165693 A1 | 6/2012 | Williams | |
| 2012/0223403 A1 | 9/2012 | Keller, III | |
| 2015/0035546 A1* | 2/2015 | Wang | G01N 15/1459 324/638 |
| 2018/0172694 A1* | 6/2018 | Farokhzad | G01N 33/6803 |
| 2020/0209062 A1* | 7/2020 | Fruehling | G01J 3/433 |

OTHER PUBLICATIONS

Apr. 19, 2013, Walter J. Keller and Bogdan Pathak; Advanced Detection of Electronic Couterfeits; Apr. 19, 2013; Nokomis, Inc.

* cited by examiner

*Primary Examiner* — Matthew D Krcha
*Assistant Examiner* — Austin Q Le
(74) *Attorney, Agent, or Firm* — AP Patents; Alexander Pokot

(57) ABSTRACT

A rapid virus and pathogen detector using RF and Dielectric Spectroscopy. The targeted virus or pathogen is identified by active illumination by RF energy and analysis of the response RF signal.

14 Claims, 13 Drawing Sheets

RF RAPID DIAGNOSTICS OF INFECTION AND CONTAMINATION

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

RELATED APPLICATIONS

This application is related to U.S. Provisional Patent Application Ser. No. 63/033,895, filed on Apr. 2, 2020, is incorporated by reference herein in its entirety.

BACKGROUND

This application is in the field of RF Spectroscopy and Dielectric Spectroscopy as applied to biological samples including viruses. When exposed to RF radiation viruses and other biological materials affect the spectrum because of their dipoles, structure, and permittivity, and reflectivity. By examining each of the spectra, permittivity and RF radiation separately or in combination the presence of targeted viruses and pathogens is detected.

BRIEF DESCRIPTION OF THE INVENTION

The technical problem is to rapidly detect the presence of a target virus without reliance on detecting antibodies, genetic material, or proteins through chemical methods. These methods identify antibodies or using a Polymerase Chain Reaction (PCR) multiplying the genetic material. These methods require a nasopharyngeal swab and are ineffective in detecting a virus outside of the closely controlled setting. The present application using Dielectric and Rotational Spectroscopy permits identification of the virus outside of the closely controlled swab sample such as on surfaces as well as detection of indicators of infection. The present application can also be used to calculate the viral load, which is correlated with the severity of disease.

The device has a sample holder to receive a sample. It can have a plurality of shapes to accommodate the type of sample and the RF transmission and reception. The sample holder can be configured in a pyramidal shape, cube, canonical shape or tapered shape, a container in which gas is evacuated, that is rectangular, cube, cylindrical, spherical. Each of these shapes are contemplated to provide different electromagnetic properties. The preferred embodiment is a tapered chamber with a tapered septum.

In one embodiment, the invention uses a swappable sample holder for the sample to be tested. That is that the sample holder can be swapped depending on the application. The device can take a sample directly from the patient to be tested, from a nasal swab, from a surface, or from the environment. The holder has transmitting and receiving antenna either within or without the sample holder. One antenna can be used as both the transmitting and receiving antenna. In the case of a single antenna, separate transmit and receive chains are described below. However, separate transmit and receive antennas are also contemplated.

In another embodiment, the invention will collect breath exhaled into a mouthpiece, in fluid communication with a measurement chamber that is under vacuum conditions, preferably −40 kPa or lower. The transmit and receive antennas are positioned such that the measurement chamber is directly between the transmit and receive antennas. One embodiment of the measurement chamber would have a pin hole aperture through one wall and vacuum exhaust through another wall pulling the breath sample through the pin hole aperture.

The sample is illuminated with RF radiation. The receiving antenna receives the electromagnetic energy that interacts with the sample and sample holder. The receiving antenna is connected to a Low Noise Amplifier (LNA) that is connected to a sensitive RF receiver, and a plurality of filters. The resulting signal is transformed from the time domain to the frequency domain and converted to digital with an analog to digital converter (ADC).

The ADC is connected to a signal analysis unit that compares the resulting spectrum successively by band windows sweeping through an ultrawide bandwidth. Preferably, the ultrawide bandwidth is from 1 MHz to 200 GHz. This range is the both the RF transmission frequency range and/or the RF frequency measurement band. The device can operate in lower or higher frequency ranges, as well as in a series of one or more narrow frequency regions throughout this span. While a range of RF is preferred, a static of electromagnetic field, a single frequency, multiple frequencies, single modulated frequency, modulated, multiple frequency modulated, wideband, ultrawideband, pulsed signals, or frequency hopping, are also usable. Complex waveforms are also used in some embodiments to create a unique response from the virus preferably the electromagnetic spectrum, The signal analysis unit is connected to the ADC output. It can be implemented on printed circuit board, FGPA, single board computer.

The device is preferably used to identify a virus signature and biomarkers indicating infection or other physiological health conditions or status. An unknown sample of virus is illuminated with RF energy in the sample holder and the resulting change in electromagnetic signal is received and processed. The signature can be identified using the various filters and examining the spectra.

Unlike traditional spectra from other biological materials a virus signature is identifiable by a single or a few peaks. Signature identification and classification requires prior algorithmic training by measuring known samples of biological material. Spectral measurements are collected with and without the target to be characterized and the methods used to uniquely identify the target are then applied to spectral features that differ from the control measurement free of biomaterial. Classification of viral and biological material can be performed using one or more methods of either quantifying the spectral characteristics using frequency, amplitude, feature envelope, and/or feature shape. Classification is a problem that is also well suited for machine learning. Classification of viral and biological material by spectral response to electromagnetic energy can be performed with either method of quantifying algorithms, or machine learning individually or in combination. Machine learning algorithms allow for feature recognition that may be overlooked, or is not quantifiable with traditional quantifying algorithms. Multiple scans of the sample summed together raises the signal to noise ratio. Additionally, Wavelet Denoising cleans the signal noise. The data will be processed with sequentially applying a method of Singular Spectrum Analysis (SSA) to break down the original spectral signal into up to 100 components.

Machine learning, preferably using an unsupervised Density-Based Spatial Clustering of Applications with Noise (DBSCAN) algorithm to classify the data's components. The identified components classify the response signature to be the virus, pathogen, or peptide signature, absence of biomaterial present, or an unknown biomass contaminant. The use of multiple components increases sensitivity and reduces the probability of a false negative results.

Once a signature is characterized a measurement using the same or similar RF illumination and scanning settings of an unknown sample is performed and that signature is compared to the expected signature content of the target virus or pathogen. The result is passed to a reporting unit that reports the presence or absence of the target virus.

Similarly, the concentration of the virus will affect the dielectric response. Comparison of a dielectric response curve of a known virus sample at varied quantities to the response of an unknown sample then gives an estimate of the virus concentration.

Dielectric spectroscopy or impedance spectroscopy studies the response of a sample to an applied electric field of fixed or changing frequency. The dielectric properties of a material are described as a function of frequency regions of the electromagnetic spectrum. Thus, dielectric spectroscopy measures the dipole and the structure of molecules. The response of the biomaterial across the frequency spectrum are due to multiple physical properties, such as the dipole moment and molecular structure. This allows for a unique confirmation of the presence of the target virus, pathogen, or peptide. The multiple dielectric responses add to the selectivity of the measurement. The dielectric and RF rotational spectroscopy can be conducted together or separately.

BRIEF DESCRIPTION OF THE DRAWINGS

FIG. 16 is an illustration of a singular spectrum analysis (SSA) deconvolution of stronger order effects 1-6.

FIG. 17 is and illustration of SSA deconvolution of lower order effects 7 through 40.

DETAILED DESCRIPTION OF THE INVENTION

Figure 1:
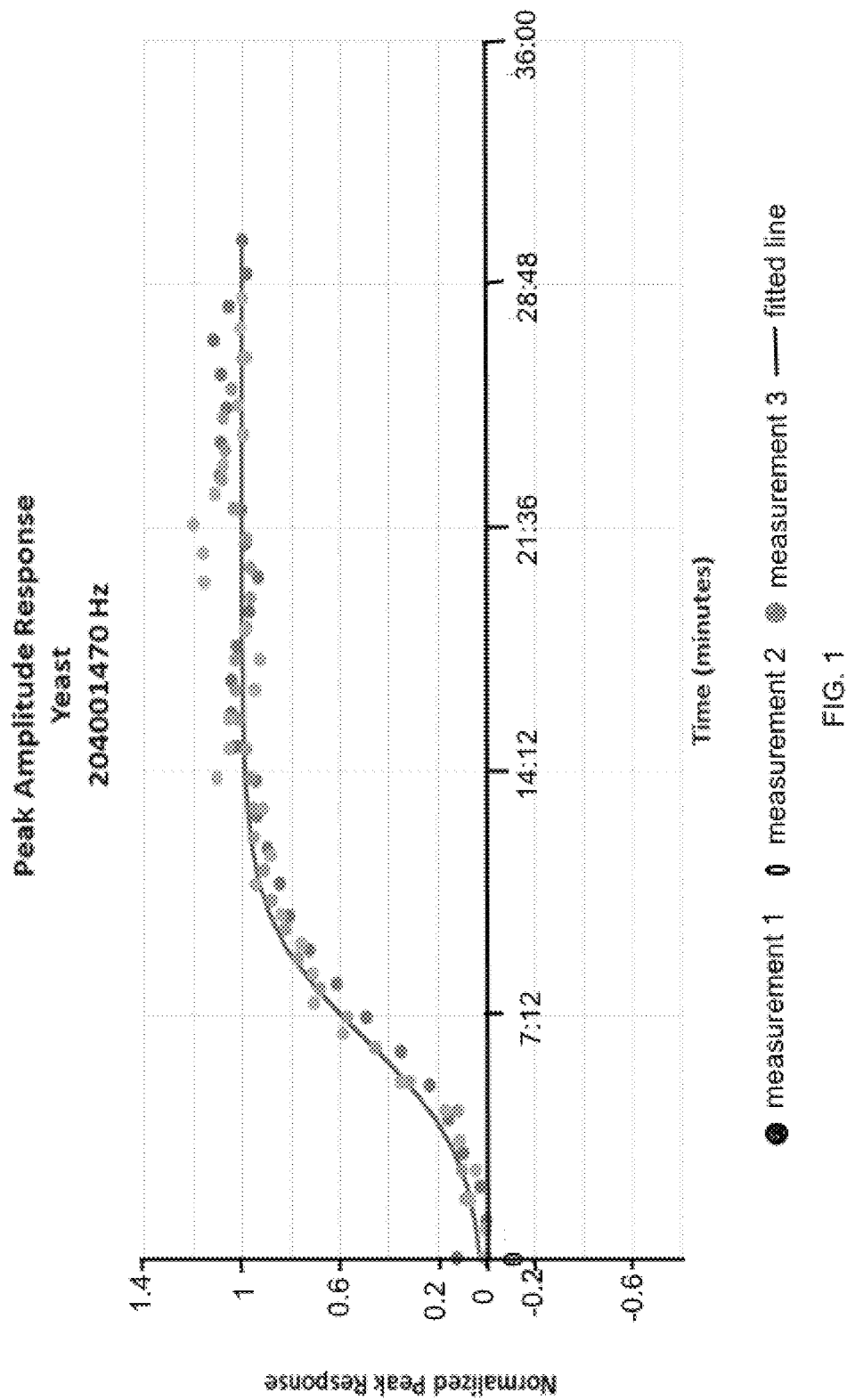
FIG. 1 is a diagram of normalized dielectric response of biologic materials changing over time.

The technical problem is to identified target viruses and pathogens. The solution is to use Dielectric Spectroscopy and RF rotational spectroscopy alone or in combination to identify the virus or pathogen fingerprint.

Dielectric Spectroscopy

Dielectric spectroscopy (DS), is a type of impedance spectroscopy, DS is also a form of electrochemical impedance spectroscopy, that examines the permittivity of a sample. DS describes the dielectric properties of a material as a function of frequency. In DS, radio and microwave frequency regions of the electromagnetic spectrum interact with materials to study their behavior at a molecular level. The interaction of alternating electric fields with dipoles possessing reorientation mobility in materials enables measurements of molecular properties from the resulting electromagnetic responses. DS determines the frequency-dependent complex permittivity of the material. It provides information on molecular dynamics as well as on important material parameters such as the static dielectric permittivity ($\varepsilon$) and DC electrical conductivity ($\sigma$). Current and voltage (amplitude and phase of an AC system) and it is also used to evaluate the dielectric properties such as dielectric constant ($\varepsilon'$), dielectric loss (tan $\delta$), etc. DS can be operated at very low frequency ranges ($\mu$Hz), where it is useful to know the state of different interfaces existing between insulation components, up to very high frequencies (THz). The real part of the permittivity or dielectric constant ($\varepsilon'$) and the imaginary part of permittivity ($\varepsilon''$) or loss factor (tan $\delta$), subjected to an alternative (AC) sinusoidal supply voltage, can be determined from the following equations:

$$\varepsilon' = \frac{C_p d}{\varepsilon_0 A}$$

$$\tan \delta = \frac{\varepsilon''}{\varepsilon'} = \frac{1}{R_p C_p \omega}$$

where $\varepsilon_0$ represents the vacuum permittivity, d represents the thickness of the sample material, A is the area of the electrode, $\omega$ indicates the angular frequency, and Cp and Rp represent the capacitance and the resistance measurements. At low frequency, the static (DC) conductivity can be extracted from the AC conductivity measurements using the formula:

$$\sigma_{ac}(\omega) = \omega \varepsilon_0 \varepsilon''(\omega) = \sigma_{dc} + K\omega^n$$

where K represents an empiric parameter and n represents the high-frequency slope of the AC conductivity ranging from 0 to 1. DS reveals the dynamic changes in the dielectric constant and scanning frequency. It provides information on the structure of matter, ion displacement, valence cloud distortion, defect displacement, state, and local space-charge electric moment orientation, etc. The movement of space charge can be comprehended using the DS technique. The acquired data provide detailed information on the electrical properties of the samples. The obtained dielectric data can be associated with other properties such as changes in gel, what is crucial for application of this approach to detect target viruses, pathogens, and peptides.

The DS is a capacitive effect. The sample in the sample holder is within a measurement chamber. The sample is positioned between opposing corresponding capacitor plates, probes, or antennas that create an electrical field from an active electrical signal. The capacitor plates, dielectric probes, or antennas either within or without the sample holder measure the permittivity.

Figure 2:
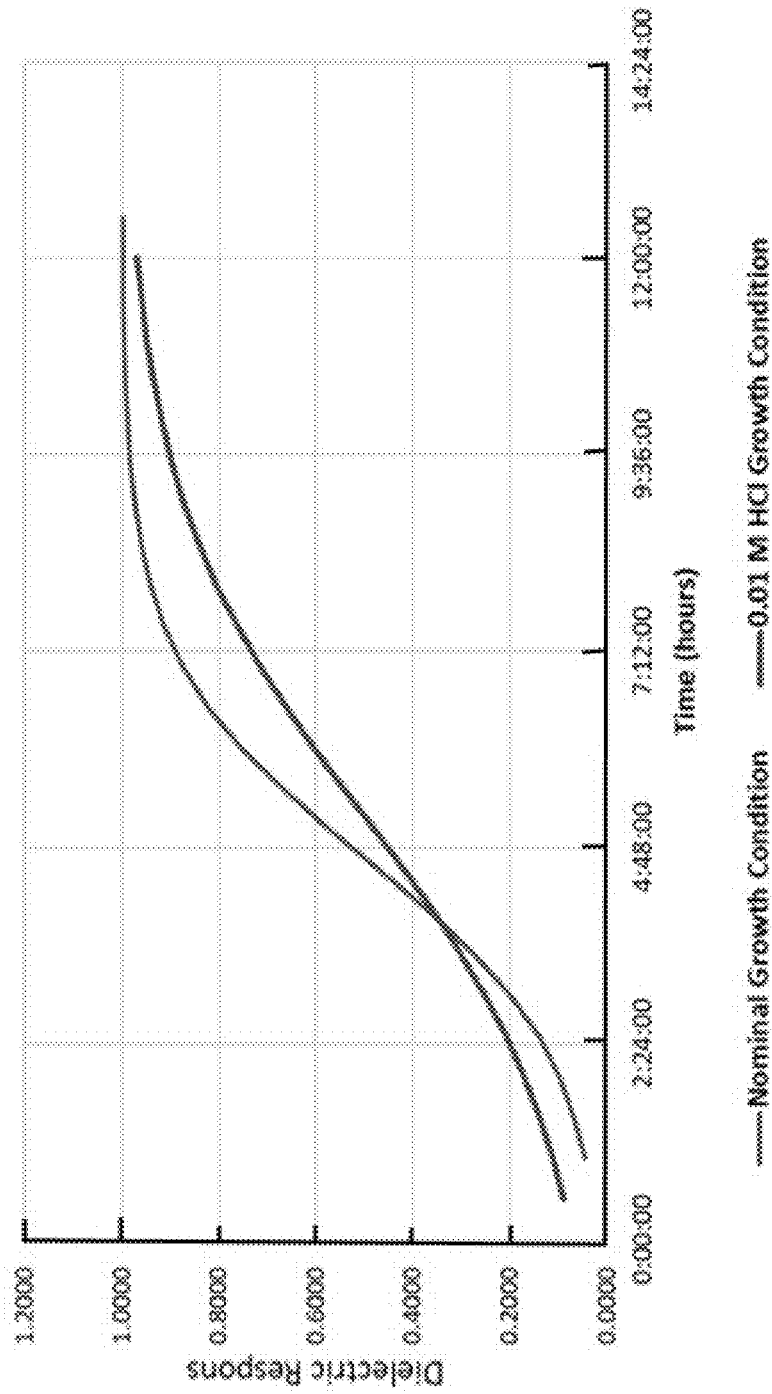
FIG. 2 is a diagram of normalized dielectric response of biologic materials changing over time in different environments.
Figure 3:
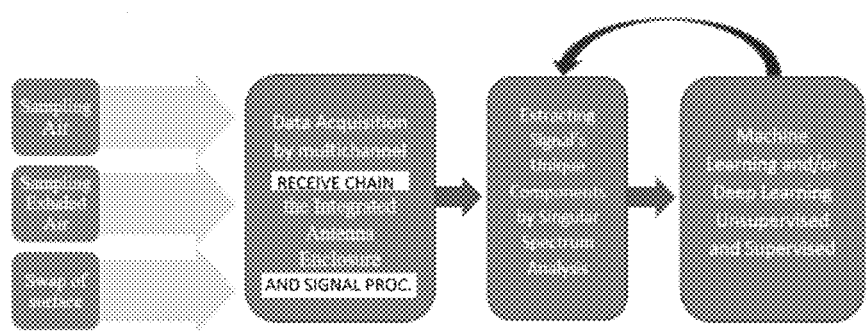
FIG. 3 is a block diagram of the fingerprint process.

FIG. 1 illustrates the normalized amplitude of a spectral peak of 204001470 Hz from an actively illuminated biologic materials over time as the biological material undergoes cell culturing. This graph of the normalized feature amplitude response over time is an illustrative graph of the dielectric response of biologic material as it physically changes. FIG. 2 is a graph that illustrates that the normalized dielectric response measurement approach of RF and dielectric response combined with a sensitive RF receiver and signal processing, described below, permits the biologic material to be identified by physical properties of the biologic material and its environment using the method described below, FIG. 3 is a block diagram of the preferred process for the identification of the target virus, pathogen, or peptide signature. The diagram in FIG. 3 shows that the same device can analyze multiple sample types. The samples are received, illuminated, a weak re-emitted signal received, connected to a sensitive RF receiver, filtered, transformed, and converted from analog to digital. The digital signal is processed. The processed digital signal is analyzed by Singular Spectrum Analysis to extract components. The components are classified by machine learning and a signature is identified for the target virus, pathogen, or peptide.

Figure 4:
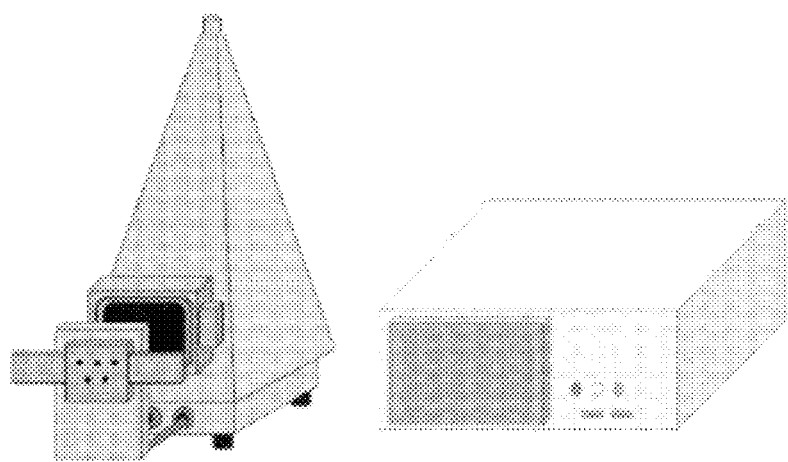
FIG. 4 is a perspective view of the device.

The preferred embodiment has a sample holder or chamber. The Bi-directional Illumination and RF Collection (BIRC) apparatus. BIRC contains a transmitting antenna and a receiving antenna. The transmitting and receiving antenna can be incorporated in the BIRC or near the BIRC, where the same antenna structure is used to do both the receiving and transmitting of the RF energy, a filter system will be employed to split the RF energy received into a transmit chain and a receive chain. The transmit and receive chain are set out below. A perspective view of the BIRC, RF receiver, signal processing and display of spectrum is shown in FIG. 4.

An alternative embodiment to the BIRC is a small vessel that has two antennas aligned with the sample in between or two parallel plates with the antenna in between. The antennas in the preferred embodiment can be at least e of Planar Inverted Antenna (PIFA), monopoles, dipoles, horn, yagi, loop antennas, compressed loop antennas, or log period antennas.

The BIRC shape can be a pyramid, cube, canonical shape, or tapered shape. Each of these configurations are contemplated as each provides different electromagnetic properties that provide benefit. The preferred embodiment is a tapered chamber with a tapered septum where the septum is driven with the illuminating RF energy to create a free field electromagnetic wave that is absorbed by the virus, bacteria, or other pathogen. The specific shape and size will be used to maximize the Q factor of the resonant measurement chamber at frequencies important to the biological test material to achieve a high Signal to Noise Ratio (SNR)

To receive a breath sample, there are one or more apertures through the BIRC chamber walls that receive the breath directly from the patient and analyze it as it flows through the BIRC. The advantage is that this enables point of care testing by collecting and storing exhaled breath directly.

In another related embodiment the breath from the subject flows into the BIRC and is held and isolated for measurement as opposed to having a continuous flow. In this configuration the breath sample can be pressurized or put under vacuum to elicit a different spectroscopic result. In addition to the RF illumination that the BIRC will facilitate the breath can also have a static electromagnetic field applied to it.

Another embodiment is to have a separate evacuated chamber that collects a sample at a distance and then is in fluid communication with the BIRC. This allows for a standoff measurement of surfaces and environments for contamination.

Another embodiment is for that receipt of a swab. A microfluidic system in the BIRC to receive fluid and swab sample. A microfluid chamber comprised of Polydimethylsiloxane (PDMS) filled with potassium chloride (KCl) (between 0.5 M and 1.5 M concentration) and Tris buffered to 7.0 pH will be exposed to allow the acceptance of swabbed viral samples. The microfluidic chamber will allow two needle electrodes to be inserted into either end of the chamber that will apply an RF AC voltage that will be supplied on one electrode with the second electrode connected to the signal analyzer to measure the current response. The dielectric properties of the solution will be extracted and used to identify the added biological material. The advantage of the microfluidic system is fine control of the fluid and sample transport.

Figure 11:
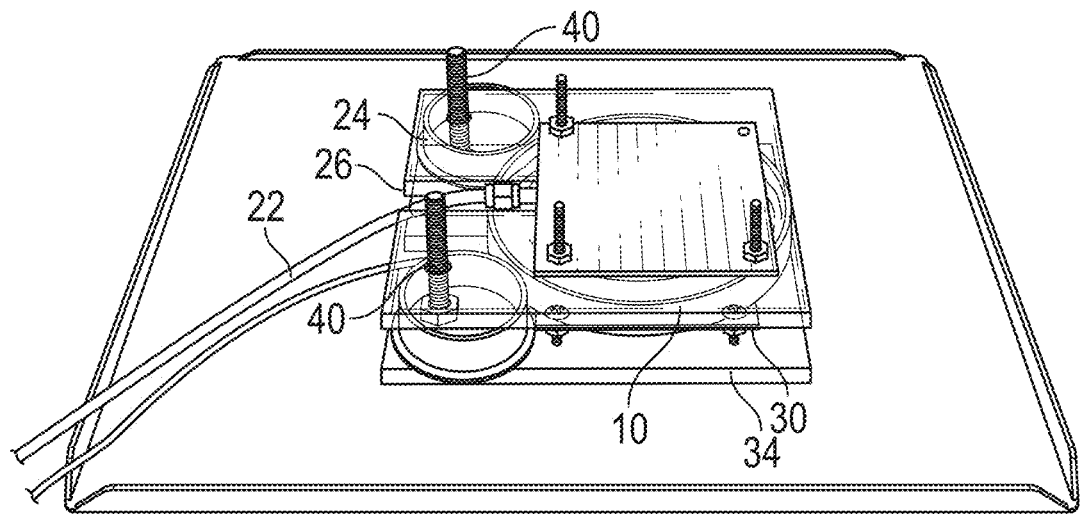
FIG. 11 is a perspective view of a sample holder with an RF integrated antenna, the sample holder is in the closed position.
Figure 12:
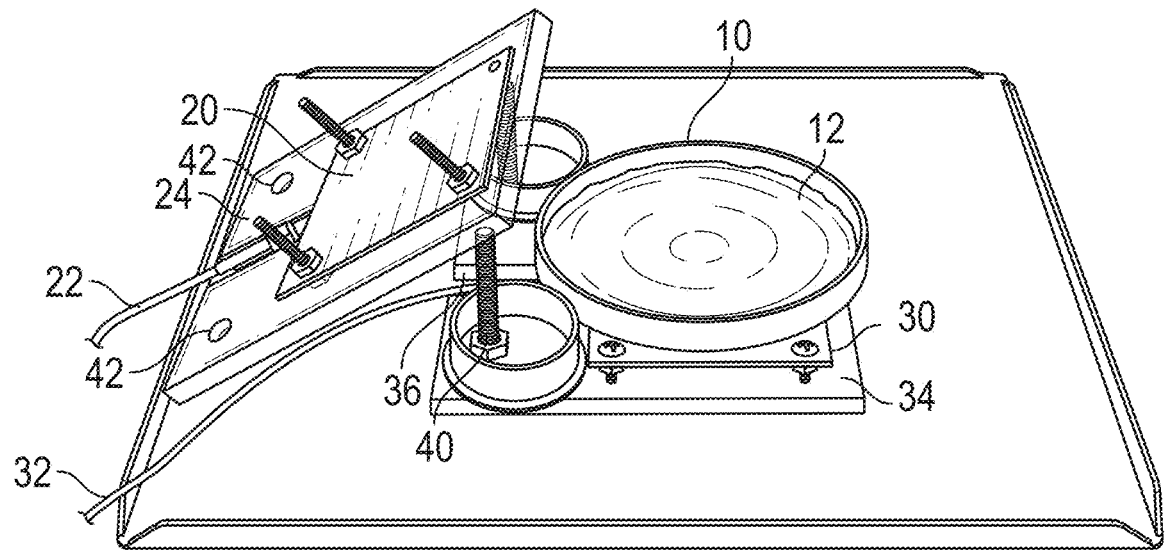
FIG. 12 is a perspective view of a sample holder with an RF integrated antenna, the sample holder is in the open position.

A simplified example of another embodiment is shown in FIGS. 11-12. A sample 12 swabbed onto a test plate 10, illustrated as an open chamber. In this embodiment, the transmitting antenna 20 and receiving antennas 30 are positioned on opposite and corresponding sides of the sample test plate 10. The transmitting antenna 20 is disposed on a surface of an antenna plate 24 and is connected to a cable 22. A cutout 26 can be provided to connect the antenna 20 to the cable 22. The receiving antenna 30 is disposed on a surface of antenna plate 34 and is connected to a cable 32. A cutout 26 can be provided to connect the antenna 30 to the cable 32. A flat capacitor plate will be centered in the BIRC that has a removable glass or plastic cover that will accept a solid material sample from a swab or other collection method. A secondary plate will preferably be lowered, from a hinge or other mechanism such that there is a registered separation distance between the plates. Pins 40 may be provided on the antenna plate 34 and apertures 42 may be provided through a thickness of the antenna plate 22 for alignment of the transmitting antenna 20 with the receiving antenna 30.

The RF signal will be applied to one of the plates from the signature analyzer and the other plate will be connected to the RF input signal of the signature analyzer. A different embodiment of this apparatus includes a small chamber under constant vacuum with a pinpoint allowing the constant intake of air. This embodiment will focus on measurements of reflected and transmitted RF signal through the chamber, providing rotational spectroscopy measurements of the incoming air sample, separately or in combination with dielectric spectroscopy measurements of the dielectric properties of the aerosolized biomaterials. This embodiment will enable physiological status determination at the Point of Care (POC) without a technician user enabling the measurement and sample handling, reducing the risk of exposure to other personnel.

The illumination by the BIRC will be at least one of a single frequency, multiple frequencies, single frequency modulated, multiple frequency modulated, wideband, ultrawideband, or frequency hopping. Complex waveforms are also used in some embodiments to create a unique response from the virus. In order to measure quantities of material that are on the order of 1 ppb or less, a combination of high sensitivity, special signal processing techniques, Q factor optimization, and proper selection of frequencies are required. In order to increase the SNR a series of acquisitions will be recorded to be combined in the signal processing phase. A high pass filter and low pass filter will be applied to each acquisition and the result of a sum over a fixed number of acquisitions.

Within the Signature analyzer contains a receive chain as follows: a sensitive RF receiver having a low noise amplifier (LNA), transceiver, signal processing hardware, processing board or single board computer, with a FFT to convert to the time domain analog signal to a frequency domain signal and Analog to Digital Converter (ADC) for a digital signal. Within the signature analyzer contains a transmit chain as follows: Signal generation and an RF amplifier or waveform generation preferably by FPGA or other computational means. An upconverter can be used, Digital to analog converter, power amplifier. A filter block that separates the received RF from the transmitted RF where there is a single transmit and receive antenna. A receiver exciter or equivalent may also be used. See FIG. 4.

In order to collect simultaneous signatures on the same sample at different frequency ranges the system employs at least one of one, two, three or four independent channels to capture the data.

Though a serial system is one embodiment where speed is not as critical to facilitate real-time throughput the data streams are parallelized, and the data processed via multiple data paths. The parallel processing can be accomplished by at least one of parallel processing using at least one of General Processing Units (GPUs), microcontrollers, CPLDs or FPGAs.

Figure 13:
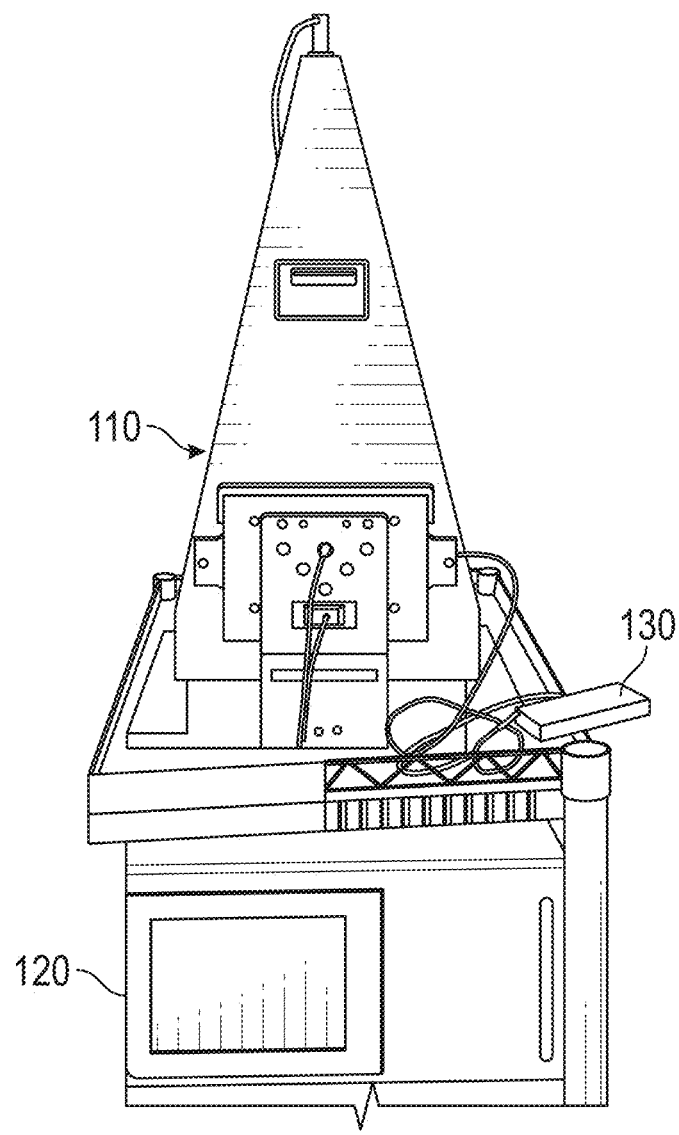
FIG. 13 is an illustration of an embodiment the signature analyzer and BIRC.
Figure 14:
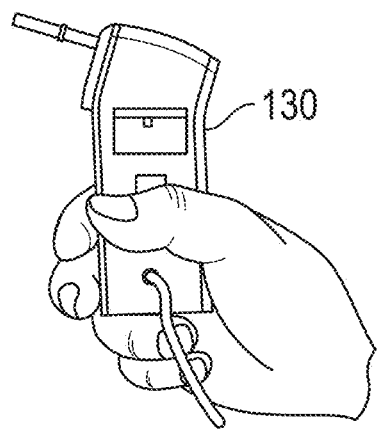
FIG. 14 is an illustration of a collection wand.

An illustration of the preferred embodiment is in FIGS. 13 and 14 where the measurement chamber is inside the BIRC 110. The measurement chamber is connected to the signal analyzer unit 120. A collection wand 130 is in fluid communication with the sample holder.

Figure 8:
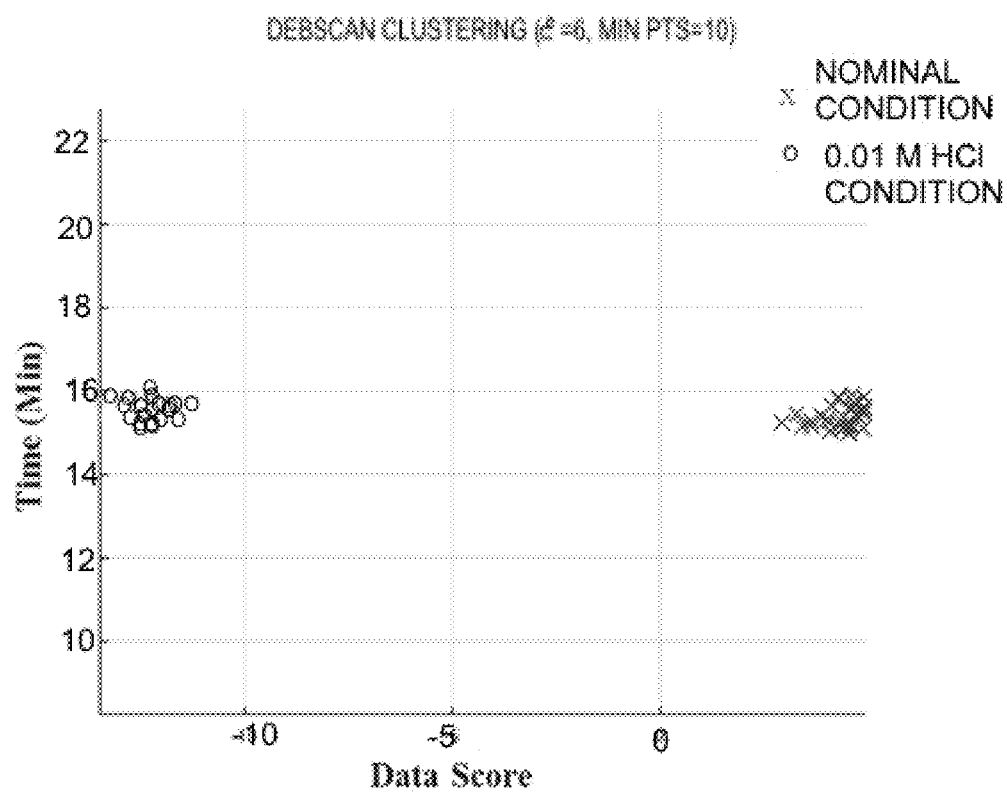
FIG. 8 is an illustrative graph of machine learning classification of biologic material normalized to time.
Figure 9:
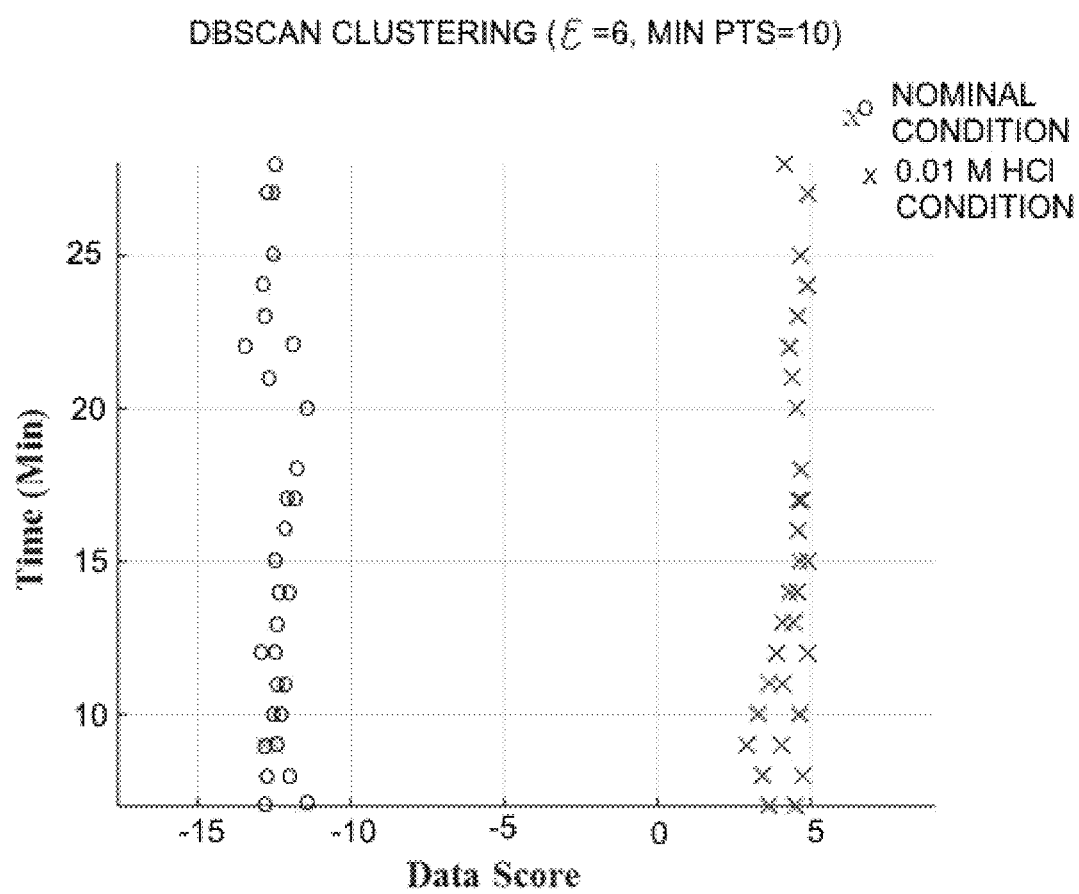
FIG. 9 is an illustrative graph of data acquired for biologic material not normalized to time.
Figure 10:
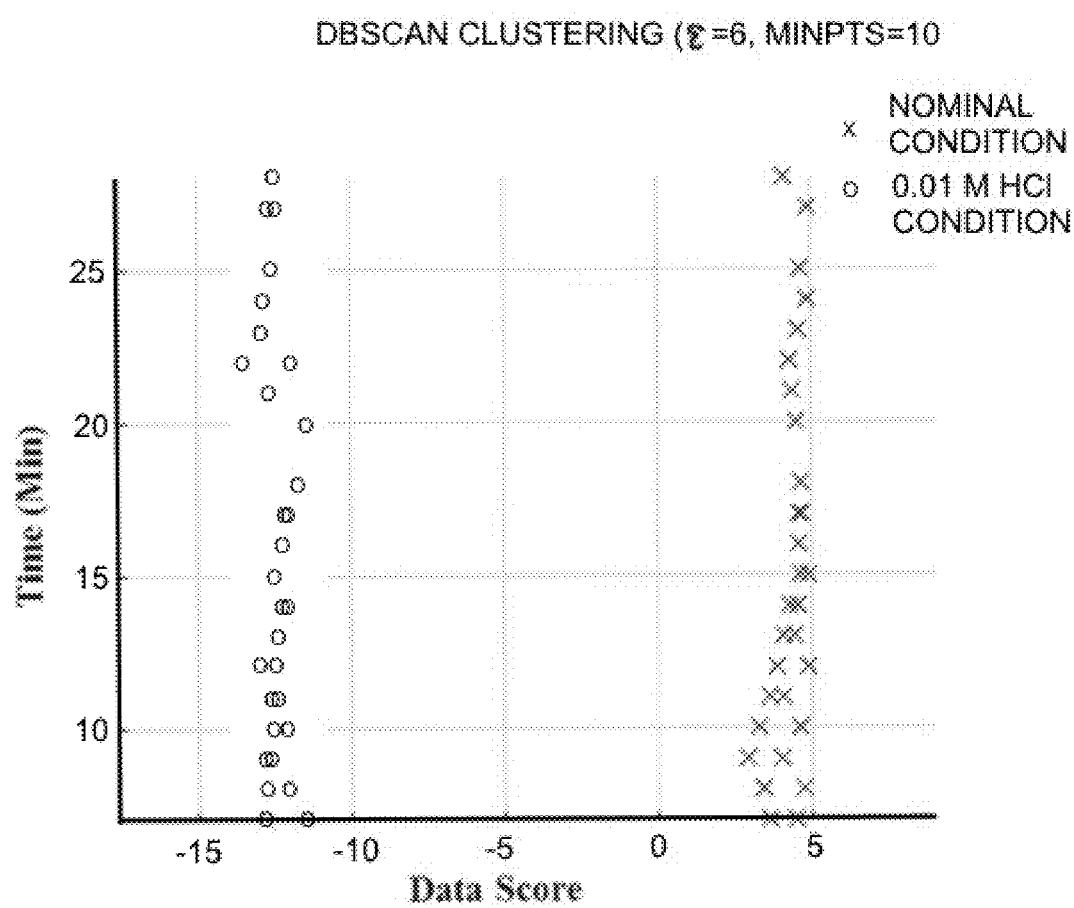
FIG. 10 is an illustrative graph of data acquired for stressed biologic material not normalized to time.
Figure 15:
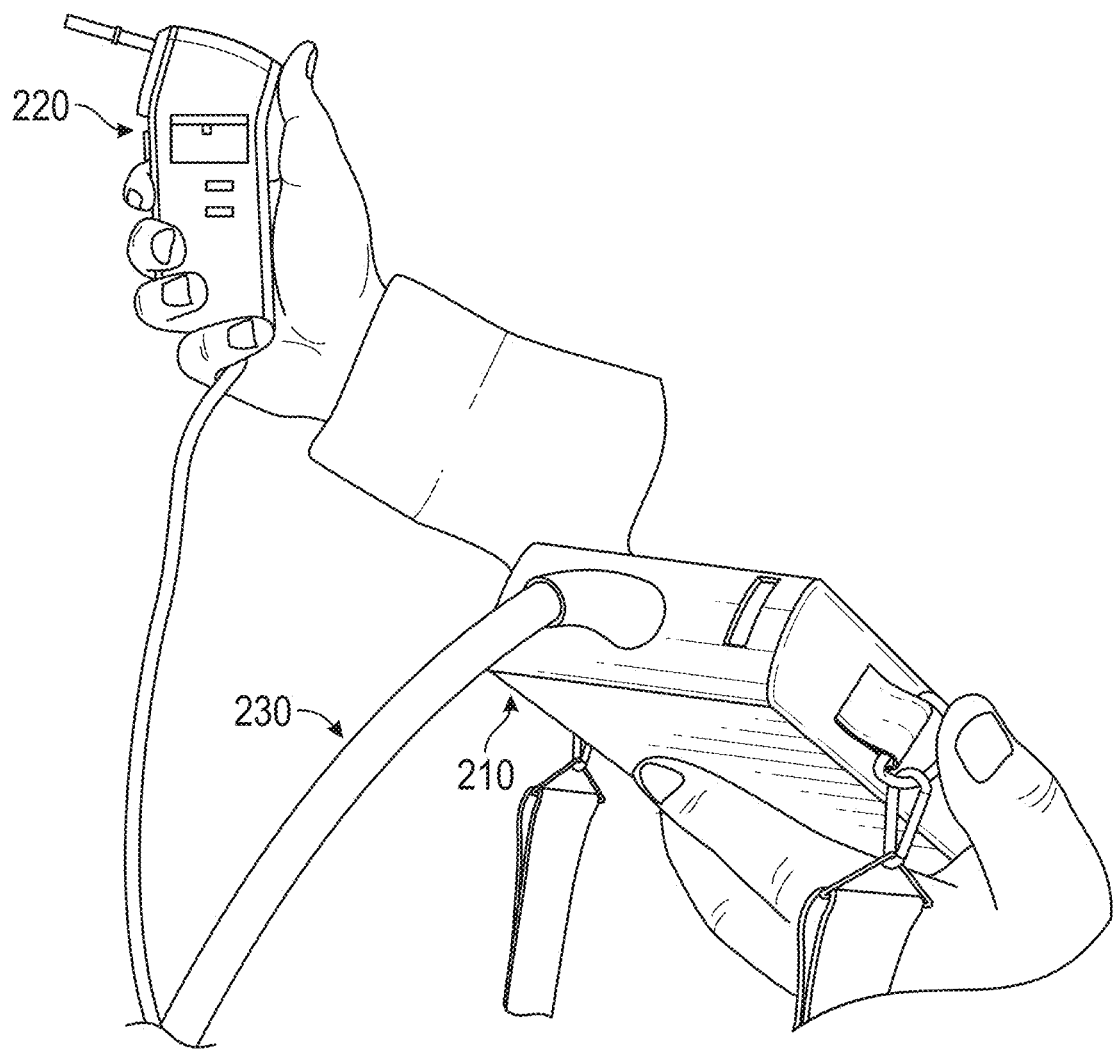
FIG. 15 is an illustration of the breath intake device.

A handheld embodiment FIG. 15 has a combined measurement and analyzer unit 210 in fluid communication with a collection wand 220 210. The process of finding the virus signature will prepare solutions containing the viruses, then place the aerosolized sample into the chamber, and place them in the BIRC which is shielded, acting as miniature anechoic chamber where the measurement chamber is separated in the embodiment. In this configuration, the Ultra-Wide Band measurements will be then taken. The data will be processed with sequentially applying a method of Singular Spectrum Analysis (SSA) to break down the original spectral signal into up to 100 components for an analysis of a variety of extremely complex spectral signals with some having Signal to Noise Ratio of −20 dB to extract unique components. At the next step of analysis selected components will be subject to a machine learning method of DBSCAN. DBSCAN is "unsupervised" method of classification and identification of unique features in the data, see FIG. 3. An illustration of the results of DBSCAN is seen in FIGS. 8-10. The example shows the clustering of data of biologic material that had a modified physical structure due to its environment. The separation of data is revealed through the density spatial clustering. The 100 or more components of complex spectra is especially suited for machine learning.

FIGS. 16-17 illustrates how SSA components, once deconvoluted, can be summed together linearly to observe stronger order effects such as water in SSA components 1 through 6 in FIG. 16, and lower order effects such as the virus response in components 7 through 40 in FIG. 17. One of the viruses has a strongly different response to the electromagnetic field than water, as measured by the Mahalanobis Distance of Water to M13 of 14.3 compared to Water to Lambda standard of 122.3 in FIG. 17. The responses of the individual viruses are more similar than either to water with a Mahalanobis Distance of M13 to Lambda standard of 8.4. Using the described signal processing the M13 sample has clear spectral features that can be separated from baseline responses in frequency space.

Figure 5:
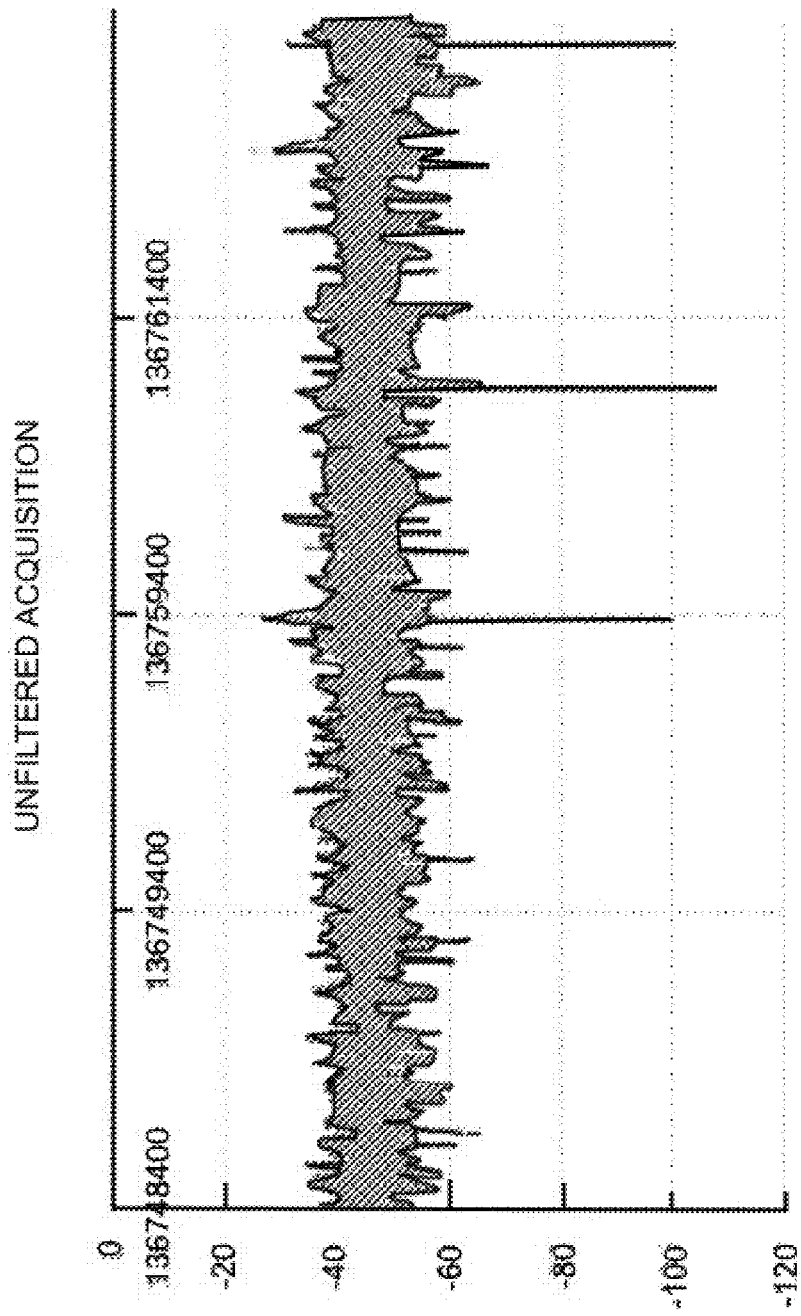
FIG. 5 is a graph of unfiltered spectra.
Figure 6:
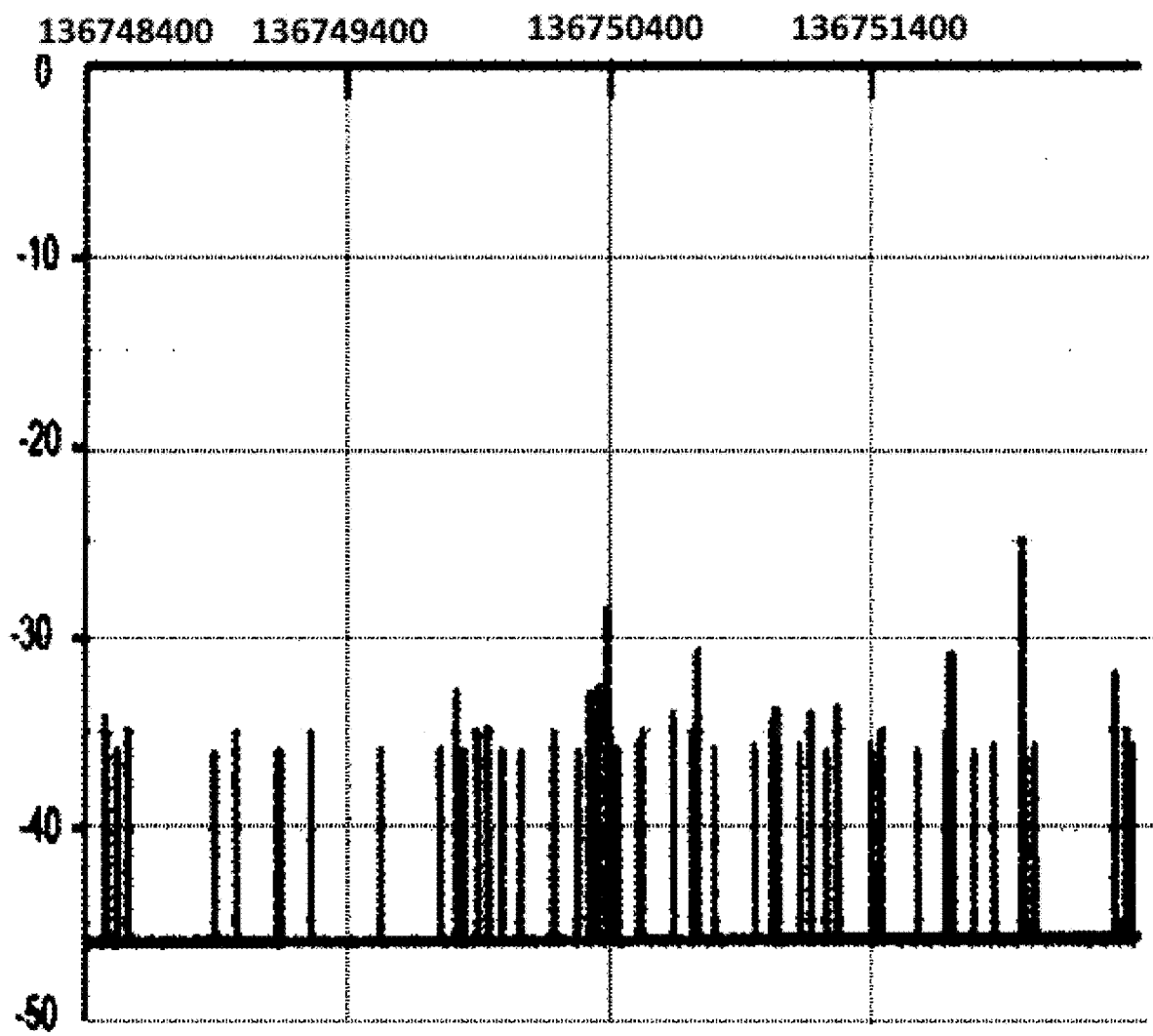
FIG. 6 is a graph of filtered spectra.
Figure 7:
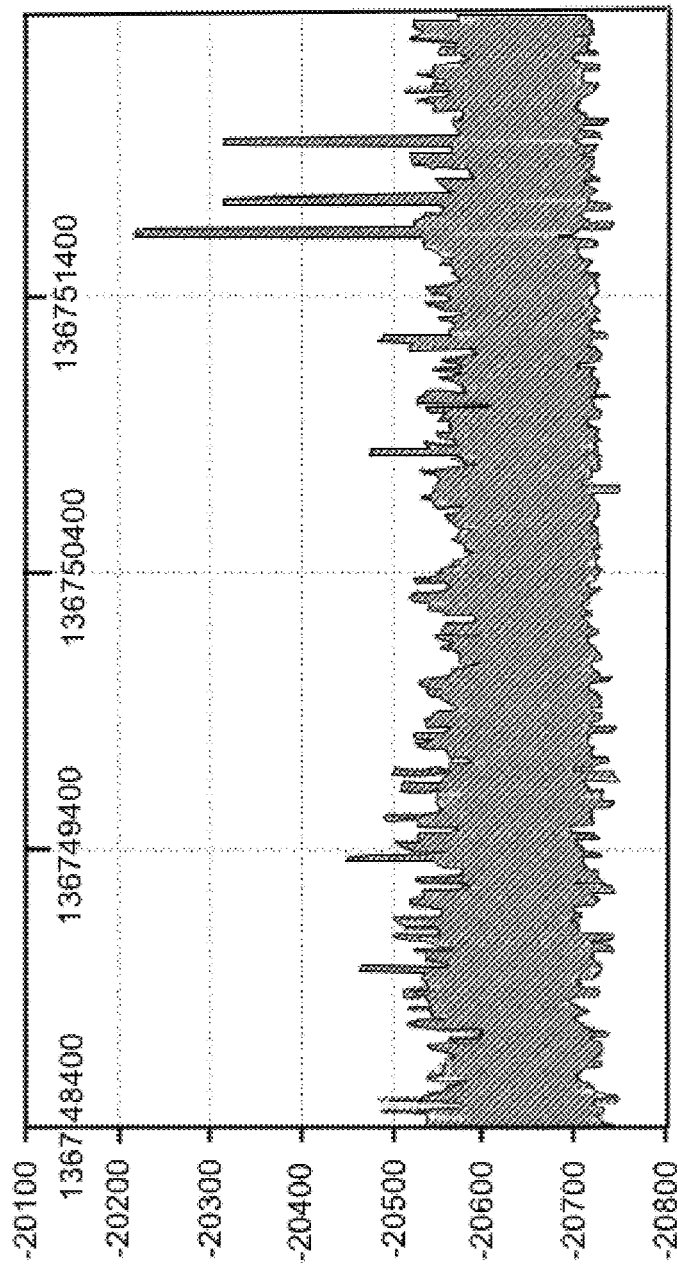
FIG. 7 is a graph of summed filtered acquisitions.

The signal to noise ration can be further increased by apply low pass and high pass filters to multiple signal acquisitions and then summing the results. An illustration of the process is shown by taking an unfiltered signal acquisition as shown in FIG. 5 and filtering that acquisition as shown in FIG. 6. By taking multiple acquisitions, as shown in FIG. 7. The multiple acquisitions of signal allow for a cleaner result from weak re-emitted signals. The resulting multiple acquisition allows a separation of the weak signal from the noise floor. Taking the device and structure described, the method is used to detect viruses, pathogens, and peptides in samples. A sample is received in a sample holder. The samples include gaseous samples directly from the person to be tested, swabs, or remotely collected sample. A liquid sample from tears or blood can also be received. The sample holder needs to be secure as too not contaminate the persons using the device, the device, or the environment. A vacuum can be applied to transport the sample into the sample holder. Also, a sample can be transported and presented to testing with a microfluidics system.

The sample is illuminated with RF radiation from an RF transmitting antenna. The antenna can be integrated into the sample holder or near the holder. The transmit antenna can also serve as a receive antenna with the transmit and receive chains described above.

A biological sample that is acted upon by an incident changing electromagnetic field will alter the electromagnetic field based on its dielectric properties which will affect the electromagnetic signal of the receive antenna. The receive antenna can be the same antenna as the transmit antenna or a separate antenna. The receive antenna is integrated into the sample holder or near the sample holder.

The received analog signal from the sample is amplified with a low noise amplified, tuned, filtered, transformed, and converted from analog to digital as described above.

A target virus, pathogen, or peptide has a spectrum signature. Illuminating a known sample as described above produces a spectrum. The spectrum is subject to analysis. The filtering allows for analysis of distinctive spectra shape and amplitude. The signal analysis unit permits identification of the target virus, pathogen, or peptide and with the dielectric properties the concentration of the target.

Creating a target virus, pathogen, or peptide spectrum signature, then allows comparison to an unknown sample. Comparing the response digital signature against the target virus, pathogen, or peptide spectrum signature by the signal analysis unit. The result of the comparison is the identification. The identification or lack of identification, a negative result is then reported.

The inclusions of one embodiment is not meant to exclude another embodiment. It will apparent to one with knowledge of the art that there are equivalent devices and methods. Further, it is not intended to invoke section 112(f) as a means for claim.

We claim:

1. A method, comprising the steps of:
   a. receiving a sample in a sample holder, including receiving the sample holder in a measurement chamber comprising a tapered chamber with a tapered septum;
   b. illuminating the sample with a radio frequency (RF) radiation;
   c. receiving a response RF signal by from the sample;
   d. amplifying, with a low noise amplifier (LNA), the response RF signal;
   e. tuning the response RF signal;
   f. filtering the response RF signal;
   g. converting, with analog to digital converter (ADC), the response RF signal from an analog form to a digital form;
   h. transforming the response RF signal from a time domain to a frequency domain;
   i. breaking down, with a signal analysis unit connected to ADC, the response RF signal into components by sequentially applying a singular spectrum analysis (SSA);
   j. analyzing, with the signal analysis unit, selected components with unsupervised Density-Based Spatial Clustering of Applications with Noise (DBSCAN); and
   k. comparing, with the signal analysis unit, a digital spectrum signature of the response RF signal against a target virus spectrum signature or against a target pathogen spectrum signature.

2. A method, comprising the steps of:
   receiving a sample in a sample holder within a measurement chamber including a tapered chamber with a tapered septum;
   transmitting, with a transmitting antenna, a radio frequency (RF) radiation toward the sample;
   receiving, with a receiving antenna, a response RF signal from the sample;
   analyzing, with a signal analysis unit connected to the receiving antenna through a low noise amplifier (LNA), an RF receiver and analog to digital converter (ADC), the response RF signal; and
   comparing a spectrum signature of the response RF signal against a virus spectrum signature or against a pathogen spectrum signature.

3. The method of claim 2, wherein receiving the sample comprises:
   exhaling a breath sample into a breath collection apparatus;
   pulling the breath sample through a pin aperture though one wall of the measurement chamber under a vacuum condition, the measurement chamber being in a fluid connection with the breath collection apparatus; and
   exhausting the sample with a vacuum through an aperture through another wall of the measurement chamber.

4. The method of claim 2, wherein receiving the sample further comprises receiving a breath sample through an aperture through a wall of the measurement chamber.

5. The method of claim 2, wherein each of the transmitting antenna and the receiving antenna comprises at least one of Planar Inverted Antenna (PIFA), monopoles, dipoles, horn, yagi, loop antennas, compressed loop antennas, or log period antennas.

6. The method of claim 2, wherein each of the transmitting antenna and the receiving antenna comprises a square shape.

7. The method of claim 2, further comprising positioning each of the transmitting antenna and the receiving antenna on an antenna plate and separating the transmitting antenna and the receiving antenna from each other.

8. The method of claim 2, wherein analyzing the response RF signal comprises:
   breaking down the response RF signal into components by sequentially applying a singular spectrum analysis (SSA); and
   analyzing selected components with unsupervised Density-Based Spatial Clustering of Applications with Noise (DBSCAN).

9. The method of claim 2, wherein analyzing the spectrum signature of the response RF signal comprises successively using band windows sweeping through an ultrawide bandwidth.

10. The method of claim 2, wherein analyzing the spectrum signature of the response RF signal comprises increasing a signal to noise ration of the response RF signal by applying low pass and high pass filters to multiple signal acquisitions and summing results of each acquisition.

11. The method of claim 2, further comprising cleaning a signal noise with a wavelet denoising.

12. The method of claim 2, further comprising detecting a virus in the sample without reliance on detecting antibodies, genetic material, or proteins through chemical methods.

13. The method of claim 2, further comprising calculating a viral load correlatable to a severity of a disease.

14. A method, comprising the steps of:
   a. receiving a sample in a sample holder, including:
      exhaling a breath sample into a breath collection apparatus,
      pulling the breath sample through a pin aperture though one wall of a measurement chamber under a vacuum condition, the measurement chamber being in a fluid communication with the breath collection apparatus, and
      exhausting the sample with a vacuum through an aperture through another wall of the measurement chamber;
   b. illuminating the sample with a radio frequency (RF) radiation;
   c. receiving a response RF signal from the sample;
   d. amplifying, with a low noise amplifier (LNA), the response RF signal;
   e. tuning the response RF signal;
   f. filtering the response RF signal;
   g. converting, with analog to digital converter (ADC), the response RF signal from an analog form to a digital form;
   h. transforming the response RF signal from a time domain to a frequency domain;
   i. breaking down, with a signal analysis unit connected to ADC, the response RF signal into components by sequentially applying a singular spectrum analysis (SSA);
   j. analyzing, with the signal analysis unit, selected components with unsupervised Density-Based Spatial Clustering of Applications with Noise (DBSCAN); and
   k. comparing, with the signal analysis unit, a digital spectrum signature of the response RF signal against a target virus spectrum signature or against a target pathogen spectrum signature.

* * * * *